United States Patent [19]

Densert et al.

[11] Patent Number: 4,971,076
[45] Date of Patent: Nov. 20, 1990

[54] METHOD OF VENTILATING THE MIDDLE EAR BY MEANS OF A VENTILATION TUBE WHICH CAN BE APPLIED IN THE TYMPANIC MEMBRANE

[76] Inventors: Barbara Densert; Ove Densert, both of Broddesonsgatan 22, S-302 34 Halmstad, Sweden

[21] Appl. No.: 459,447

[22] Filed: Jan. 2, 1990

Related U.S. Application Data

[63] Continuation-in-part of Ser. No. 249,408, Sep. 26, 1988, abandoned.

[30] Foreign Application Priority Data

Sep. 25, 1987 [SE] Sweden .................................. 8703694

[51] Int. Cl.$^5$ ............................................. A61M 27/00
[52] U.S. Cl. ..................................... 128/898; 606/109; 604/264
[58] Field of Search ................ 128/898, 864; 604/264, 604/266, 272; 606/109, 108; 623/10, 12

[56] References Cited

U.S. PATENT DOCUMENTS

| | | | |
|---|---|---|---|
| 3,700,380 | 10/1972 | Kitrilakis | 623/12 X |
| 3,871,380 | 3/1975 | Heros | 604/264 |
| 3,976,081 | 8/1976 | Lapidot | . |
| 4,094,303 | 6/1978 | Johnston | 623/10 X |
| 4,712,537 | 12/1987 | Pender | 606/109 X |

FOREIGN PATENT DOCUMENTS

| | | |
|---|---|---|
| 0202031 | 4/1986 | European Pat. Off. . |
| 2355644 | 11/1972 | Fed. Rep. of Germany . |
| 2365484 | 3/1975 | Fed. Rep. of Germany . |

Primary Examiner—Michael H. Thaler
Attorney, Agent, or Firm—Ostrolenk, Faber, Gerb & Soffen

[57] ABSTRACT

Ventilation tube without protruding flanges, intended for ventilation and drainage of the middle ear by temporary implantation into the tympanic membrane, said tube having a micro-pitted titanium exterior surface with at least a number of micro-pits with a diameter of about 2-20 micrometer and a depth of 5-80 micrometer, as well as method and use of such ventilation tube.

3 Claims, 1 Drawing Sheet

METHOD OF VENTILATING THE MIDDLE EAR BY MEANS OF A VENTILATION TUBE WHICH CAN BE APPLIED IN THE TYMPANIC MEMBRANE

This is a continuation of application Ser. No. 249,408, filed Sept. 26, 1988, and now abandoned.

FIELD OF THE INVENTION

The invention relates to a method of ventilating the middle ear by means of a tube temporarily implanted in the tympanic membrane, the tube having functional length and being provided with an exterior surface of titanium designed to abut the tympanic membrane, a ventilation tube for performing the method and the use of such a tube.

PRIOR ART

As is known, the function of the middle ear is to transmit sound energy from the surroundings to the inner ear where these sound signals undergo complicated interpretation processes. When sound energy is carried from a medium in the surroundings (air) to another medium (liquid) in the inner ear, having considerably higher impedance, the sound signal must be amplified. This amplification occurs in the middle ear with the aid of the auditory bones and the shape and function of the related structures. If the combined transmission and amplification mechanism is to function and the hearing remain satisfactory, the structures of the middle ear as a whole must retain the normal impedance. A fundamental condition for this is that the middle ear is normally ventilated.

However, one of the most common ear complaints, especially among children, is caused by liquid collecting in the middle ear, resulting in reduced hearing. Puncturing the tympanic membrane and inserting a ventilation tube is thus one of the operations most known and most often performed.

The method of ventilating the middle ear through the tympanic membrane has long been used (Armstrong B. V. 1954). In USA alone around a million operations of this type, with insertion of ventilation tubes in the tympanic membrane, are performed annually. About 5 million ventilation tubes are used annually in West Europe, USA and Japan, and most of these tubes are applied in the tympanic membranes of children under anaesthetic.

The body's natural response to the introduction of foreign material is inflammation, massing of tissue and subsequent rejection. In principle this applies to all materials not occurring naturally in the human body.

The main problem connected with such ventilation tubes has therefore been their rejection from the tympanic membrane, partially caused by the massing of reaction products, often resulting in the tube becoming clogged. When using the known tubes, therefore, it has been impossible to ensure that the tube will continue to function over a long period of time, which is necessary if the therapeutic effect is to be achieved. Repeated operations, often under anaesthetic, were previously necessary, entailing considerable suffering, especially in the case of children, as well as incurring high costs for society.

Attempts have been made previously to prevent such ventilation tubes, mostly manufactured of titanium, from being rejected too rapidly from the tympanic membrane, by providing them with flanges or the like protruding from their outer surface. Such protruding flanges were arranged primarily at the end of the tube located within the tympanic membrane during use see for instance the technique described in U.S. Pat. No. 3 976 081.

Although offering a certain improvement in retention of the ventilation tube, such constructions cause unnecessarily large perforations in the tympanic membrane when the tube is applied, as well as a complicated operation to remove it. Ventilation tubes with such securing flanges thus require complicated surgery from a technical point of view, as well as increasing the chances of complications in the form of an increased number of permanent perforations in the tympanic membrane and ingrowth of stratified epithelium with destructive diseases of the ear in the form of cholesteatoma.

It is also known that titanium has unique biocompatible properties through its ability to adjust to the body tissues. Various clinical areas of application have been tested with success. Fixtures of various types have been used for securing different types of prostheses to the bones.

OBJECT OF THE INVENTION

The main object of the present invention is to eliminate the above-mentioned difficulties and drawbacks of the known technology and create optimal conditions for the easiest possible operative incision when applying the ventilation tube in the tympanic membrane, to eliminate the risk of rejection, thereby avoiding additional operations, to considerably reduce the risk of clogging in the actual ventilation channel and to reduce damage of the body tissue to an absolute minimum when applying and removing the tube from the tympanic membrane.

SUMMARY OF THE INVENTION

According to the invention it has now proved possible to achieve this object if the end portion of the ventilation tube designed for cooperation with the middle ear or the tympanic membrane, respectively, has no protruding securing flanges and if the exterior surface of the ventilation tube is provided with at least a number of micro-pits having a depth of approximately 5–80 micrometer and a diameter of 2–20 micrometer, to induce delayed rejection of the tube. (1 micrometer = 1 $\mu m = 10^{-6}$ m).

The micro-pitted exterior surface of the ventilation tube thus achieved, where the micro-pits can in principle be compared to the cratered surface of the moon, has thus proved to offer suitable delay in the rejection effect of the ventilation tube applied in the tympanic membrane, without risk of the exterior of the tube becoming fused with the tissue of the tympanic membrane. Clinical tests show that the micro-pitted titanium surface according to the invention results in automatic rejection of the tube after a suitable period necessary for the healing process.

According to a suitable embodiment of the invention the depth of the micro-pits is 5–25, preferably 10–20 micrometer and their diameter 2–10, preferably 4–8 micrometer.

To prevent clogging of the inner ventilation channel this should be made of a material having minimum affinity to body secretions and body tissue. This can be achieved by varnishing the inner defining surfaces of the ventilation channel.

According to a suitable embodiment of the invention the ventilation tube consists of a titanium tube.

Alternatively a plastic tube with a continuous coating of titanium oxide on the exterior may be used, the thickness of the titanium layer suitably being 100-1000 A.U., preferably about 500 A.U. (1 A.U. = 1 nm = $10^{-9}$).

The plastic material is suitably fluoroplastic, in which case the exterior of the plastic tube is provided in known manner with the micro-pitting proposed according to the invention, after which the micro-pitted plastic surface is coated with titanium in known manner.

According to another embodiment of the invention the ventilation tube may be provided with an insertion piece at the end facing the middle ear when applied. Alternatively, to facilitate its application in the tympanic membrane, the ventilation tube may be cut at an angle at the insertion end. This gives the advantage that the tube can be inserted in the tympanic membrane without damaging the radial collagen fibres, thus greatly reducing traumatization of the membrane and subsequent scarring during the healing process.

If the ventilation tube consists of a plastic material, fluoroplastic is used as mentioned above, or some other polymer material such as segment-polymerized polyurethane in which the polar "hard" and non-polar "soft" chemical segment compositions can be selected to give the desired effect, the hard segments giving the physical properties and the soft segments giving bipolarity and causing phase separation.

The invention thus also relates to a method of eliminating the rejection of ventilation tubes for drainage and ventilation of the middle ear, said tubes having been temporarily positioned by perforation of the tympanic membrane. The invention also comprises the use of a ventilation tube provided with a micro-pitted exterior surface of titanium, said micro-pits having a depth of 5-80 micrometer and a diameter of 2-20 micrometer, for temporary implantation in the tympanic membrane for draining and ventilating the middle ear.

BRIEF DESCRIPTION OF THE DRAWINGS

The invention will be described in more detail in the following with reference to an embodiment shown by way of example in the accompanying drawings. The invention is not, however, limited to the embodiment in the drawings, in which.

DESCRIPTION OF THE PREFERRED EMBODIMENT

Figure 1:
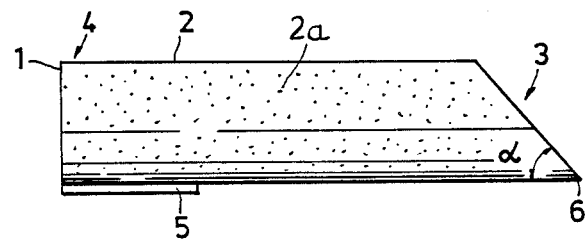
FIG. 1 shows a lateral view of a ventilation tube according to the invention.
Figure 2:
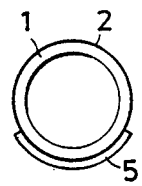
FIG. 2 shows an end view of the tube shown in FIG. 1.

In the example shown in the drawings, the ventilation tube consists of a plastic tube 1, with an outer coating 2 of titanium oxide. The layer 2 is preferably microscopically uniform, impermeable and continuous so that no biological material can penetrate through the layer 2 to the material of the tube 1. The plastic tube 1 has been manufactured by injection moulding and its outer surface thereafter micro-pitted 2a as described. The exterior of the plastic tube has then been provided with a thin, continuous layer of titanium oxide, with a layer thickness of about 500 A.U. This titanium oxide layer is also applied in known manner. The micro-porous structure on the exterior of the plastic tube is thus covered with a layer of titanium oxide, while still retaining the micro-pitting. The micro-pits according to the invention may be of any configuration, not necessarily circular. As mentioned previously, the micro-pitted surface may be substantially compared to the cratering on the moon surface and the number of micro-pits may vary according to the friction desired between the ventilation tube and the tympanic membrane.

The insertion end 3 of the ventilation tube 1 is cut along a plane to a point 6 with a top angle $\alpha$ preferably within the interval 50°-60°.

At the opposite end 4 of the tube is a shoulder 5, preferably located in the same angular position as the point 6, so that when the tube is applied the position of the shoulder 5 indicates the position of the tip of the tube. The shoulder 5 may start at the end 4 of the tube 1 and extend a distance of about 0.5 mm along the tube towards the end 3, said shoulder having a uniform thickness of 0.1 mm, for instance, in the radial direction of the tube, and extending over about ⅓ of the way around the tube 1.

The total length of the tube may be about 5±1 mm. The outer diameter of the tube is suitably ≦1.2 mm and its inner diameter may suitably be about 0.9 mm.

As mentioned earlier in the description, the ventilation tube may also be made entirely of titanium with the crater-like outer surface according to the invention within the interval specified in the claim with respect to the depth and diameter of the recesses or pits.

We claim:

1. In a method of installing a ventilation tube intended for drainage and ventilation of the middle ear comprising inserting the ventilation tube into the middle ear, said tube having been temporarily positioned by perforation of the tympanic membrane, the improvement comprising the use of a flangeless ventilation tube having an exterior surface of titanium provided with micro-pits having a depth of about 5-80 micrometers and a diameter of 2-20 micrometers.

2. A method as claimed in claim 1, wherein a titanium tube is used as the ventilation tube.

3. A method as claimed in claim 1, wherein a plastic tube with a surface coating of titanium is used as the ventilation tube.

* * * * *